(12) United States Patent
Bender et al.

(10) Patent No.: US 8,865,605 B2
(45) Date of Patent: Oct. 21, 2014

(54) ANTIMICROBIAL COMPOSITION FOR FINISHING TEXTILES

(75) Inventors: Walter Bender, Rheinfelden (CH); Oliver Marte, Wattwil (CH); Walter Marte, Ulisbach (CH)

(73) Assignee: Sanitized AG (CH)

( * ) Notice: Subject to any disclaimer, the term of this patent is extended or adjusted under 35 U.S.C. 154(b) by 1532 days.

(21) Appl. No.: 12/518,216

(22) PCT Filed: Dec. 11, 2007
(Under 37 CFR 1.47)

(86) PCT No.: PCT/EP2007/063665
§ 371 (c)(1),
(2), (4) Date: Nov. 18, 2010

(87) PCT Pub. No.: WO2008/071681
PCT Pub. Date: Jun. 19, 2008

(65) Prior Publication Data
US 2011/0065346 A1   Mar. 17, 2011

(30) Foreign Application Priority Data
Dec. 12, 2006  (DE) .......................... 10 2006 058 956

(51) Int. Cl.
B32B 27/04 (2006.01)
B32B 27/12 (2006.01)

(52) U.S. Cl.
USPC ........................................ 442/123; 106/18.32

(58) Field of Classification Search
USPC ........................................ 442/123; 106/18.32
See application file for complete search history.

(56) References Cited

U.S. PATENT DOCUMENTS

| | | | |
|---|---|---|---|
| 4,576,728 A | 3/1986 | Stoddart | |
| 4,615,882 A | 10/1986 | Stockel | |
| 5,411,585 A | 5/1995 | Avery et al. | |
| 6,228,127 B1 | 5/2001 | Reinehr et al. | |
| 6,376,696 B1 | 4/2002 | Raab et al. | |
| 6,378,803 B1 | 4/2002 | Saiz | |
| 6,387,856 B1 * | 5/2002 | Ofosu-Asante et al. | 510/131 |
| 6,673,761 B2 | 1/2004 | Mitra et al. | |
| 6,740,626 B2 | 5/2004 | Neumiller | |
| 2004/0261196 A1 * | 12/2004 | Ghosh et al. | 8/147 |
| 2005/0182140 A1 | 8/2005 | Payne | |
| 2007/0065475 A1 | 3/2007 | Elfersy | |
| 2010/0115706 A1 | 5/2010 | Bender | |

FOREIGN PATENT DOCUMENTS

| | | |
|---|---|---|
| DE | 199 28 127 C1 | 5/2000 |
| WO | 00/78770 A1 | 12/2000 |
| WO | 2004/087226 A1 | 10/2004 |
| WO | 2005/069785 A2 | 8/2005 |
| WO | 2005/069785 A3 | 8/2005 |
| WO | 2007/135163 A1 | 11/2007 |

OTHER PUBLICATIONS

International Search Report Issued in the Corresponding International Application No. PCT/EP2007/063665, Completed on Mar. 31, 2008 and Mailed on Apr. 8, 2008.
International Search Report of PCT/EP2007/063663, mailed Apr. 25, 2008.
Mar. 25, 2011, Office Action in U.S. Appl. No. 12/518,477.
Oct. 17, 2011, Office Action in U.S. Appl. No. 12/518,477.
Jun. 19, 2012, Office Action in U.S. Appl. No. 12/518,477.
Jan. 7, 2013, Office Action in U.S. Appl. No. 12/518,477.
Jul. 12, 2013, Office Action in U.S. Appl. No. 12/518,477.

* cited by examiner

*Primary Examiner* — Lynda Salvatore
(74) *Attorney, Agent, or Firm* — J.A. Lindeman & Co., PLLC

(57) ABSTRACT

An antimicrobial composition comprising an organic antimicrobial component (K) and at least one metal salt component (M) and also, where appropriate, a solvent (L) and further auxiliary components, which comprises as organic component (K) at least one compound of the general formula (I)

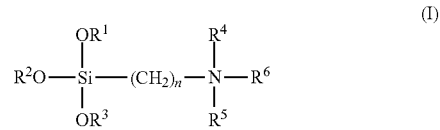

(I)

where the radicals independently have for example the following meanings:
$R^1$ is a branched or unbranched alkyl radical having 1 to 12 carbon atoms,
$R^2$ is a branched or unbranched alkyl radical having 1 to 12 carbon atoms,
$R^3$ is a branched or unbranched alkyl radical having 1 to 12 carbon atoms,
$R^4$ is a branched or unbranched alkyl radical having 1 to 18 carbon atoms,
$R^5$ is a branched or unbranched alkyl radical having 1 to 18 carbon atoms,
$R^6$ is a branched or unbranched alkyl radical having 8 to 18 carbon atoms;
n is an integer from 1 to 6,
and which comprises as metal salt component (M) at least one salt of a di- to pentavalent metal, is useful for durable finishing of textiles.

11 Claims, No Drawings

ANTIMICROBIAL COMPOSITION FOR FINISHING TEXTILES

This is a National Phase Application in the United States of International Patent Application No. PCT/EP2007/063665 filed Dec. 11, 2007, which claims priority on European Patent Application No. 10 2006 058 956.4 filed Dec. 12, 2006.

The present invention relates to an antimicrobial composition for finishing textiles, yarns and fibers, comprising an organic antimicrobial component (K) and at least one metal salt component (M) and also, where appropriate, solvent and further, auxiliary components.

Various processes are described in the prior art for finishing textiles with antimicrobial components that are said to enhance the wearing comfort of garments for example. Most textiles contain microbiologically degradable material. They are frequently either wholly or partly made of microbiologically degradable fibers, for example cotton, cellulose (e.g., viscose and Tencel), hemp, flax, linen, silk, acetate or wool. Textiles made of synthetic fibers such as for example polyester, polyacrylonitrile, polyamide (e.g., aramid, Nomex, Kevlar, nylon-6, nylon-6,6) or polypropylene are also regularly colonized by bacteria, in particular when treated with finishing agents, for example, softeners, hydrophobicizers, antistats and/or binders, or pick up microbiologically degradable material in use, for example organic substances from the environment.

Colonization with microorganisms such as bacteria can have a negative impact on the performance characteristics of textiles as well as their appearance.

The organic constituents of apocrine sweat, a liquid which is virtually odorless on emergence from the glands, are decomposed by bacteria of the skin flora. This also occurs on with textile materials which come into contact with sweat.

The small molecules such as butyric acid or formic acid which result from the degradation of, for example, long-chain fatty acids or hormones, such as testosterone for example, lead to an undesirable sweaty odor. Textiles made of synthetic fibers such as polyester or polyamide for example are particularly susceptible to bacterial degradation of sweat and therefore can have the typical unpleasant odor of decomposed perspiration after a particularly short time.

However, as will be known, colonization by microorganisms and the degradation of sweat can be inhibited by conferring an antimicrobial finish on textiles. The antibacterial finishing of textiles utilizes substances such as triclosan (a phenoxyphenol derivative) for example in the prior art or else, more recently, preparations based on silver ions. Technically, however, products comprising these substances have their limits. Disadvantages include, for example, the vapor pressure of triclosan on the tenter and the attainable wash-durability of the hitherto available silver products, particularly when no polymeric binder is applied. However, the avoidance of binders is often necessary since polymeric binders alter the hand of textiles, which is not always desired as an effect.

There is thus no composition or no one active compound which is equally suitable for all antibacterial finishes. There is therefore no adequate solution to the problem of providing a durable antimicrobial or antibacterial finish, particularly on textiles consisting wholly or partly of synthetic fibers such as polyamide or polyester.

Especially in the case of sensitive textiles, on the other hand, the need for an antimicrobial finish is quite immense, since such textiles are often used for application in the sports and leisure sector where the textile properties of these fibers are very particularly desired, but on the other hand the exposure of the textiles to sweat is very considerable by the very nature of sport exertions. Moreover, food, heat and moisture, which are fundamental bases for the growth of bacteria, arise particularly in the case of sports textiles.

In addition to apparel textiles, there are more and more uses of synthetic fibers such as polyamide and particularly polyester in the sector of home textiles, where such fibers are often used in the form of microfibers. Examples of such uses of synthetic fibers are microfiber cloths for cleaning, terry or else upholstery fabrics.

In addition to the antibacterially active substances already mentioned, the use of quaternary ammonium compounds (known was "quats") for the antibacterial finishing of textiles has been described. Substances of this class often cover a broad microbial spectrum to excellent effect.

This class of substances is described in detail in Karl Heinz Wallhäusser, Praxis der Sterilisation Desinfektion—Konservierung, 5th edition, Georg Thieme Verlag Stuttgart, New York 1995, page 586 ff. It has long been known that quaternary ammonium compounds have a bactericidal effect when at least one of the four substituents on the quaternary nitrogen has a chain length of 8 to 18 carbon atoms, preferably a chain length of 12 to 16 carbon atoms.

The other substituents can be, for example, straight or branched alkyl radicals or radicals comprising heteroatoms or radicals comprising aromatics. Frequently, one or more benzyl radicals are also attached to the quaternary nitrogen in the molecule. Good results were also obtained with quaternary ammonium compounds having two methyl groups, one n-alkyl group having between 10 to 18 carbon atoms and one 3-trimethoxysilylpropyl groups.

Quaternary ammonium compounds have the positive property of being readily soluble in water. This property fits in very well with the aqueous application in the industrial finishing operation of the textile industry. At the same time, however, this property also leads to such compounds being quickly washed off the textiles, since their adherence to textiles is primarily possible by means of Van der Waals forces with or without ion pair bonds To improve wash durability on textiles, the precursors of the quats, namely tertiary amines, have been quaternized with 3-chloropropyltrimethoxysilane. When this quaternization is carried out in the solvent methanol, this reaction has already been known for decades.

The quaternization can also be effected with octadecyldimethylamine in methanol, and then leads to a product which is suboptimal with regard to antibacterial performance. The main disadvantage of this product is the solvent methanol which, because of its properties, leads to massive curtailments in use in the textile industry.

Among commercially available products there are, for example, products having a trimethoxysilylpropyl group on the quaternary nitrogen, which are obtainable from the reaction with didecylmethylamine or with tetradecyldimethylamine or from the reaction with octadecyldimethylamine. The solventless quaternization of amines is described in DE-A 199 28 127 for example.

Polyester textiles have hitherto been finished with a formulation comprising the active compound dimethyltetradecyl[3-(trimethoxysilyl)]propylammonium chloride, the formulation being on the market as Sanitized T 99-19. The formulation comprises a 50% solution of the technical grade active compound (salt) in methyl triglycol. Methyl triglycol has the chemical formula $CH_3(OCH_2CH_2)_3$—OH.

The likewise known product Aegis AEM 5772/5 is an approximately 5% aqueous solution of the active compound dimethyloctadecyl[3-(trimethoxysilyl)propyl]ammonium chloride. Alternatively, the more concentrated active compound is also available as a solution in methyl alcohol.

Preparing the application baths gives very rapidly rise to the hydrolysis products of the active compounds, which tend to oligomerize, unless they are already present as predominantly hydrolyzed product in the commercial form.

The finishes are preferably applied to the textiles in the padding process.

When these textiles are tested by means of a count test to JIS L 1902:2002 or ASTM E 21-49, they are found to exhibit an excellent antibacterial effect. Applied to textiles composed of cellulose fibers for example, these known products find reaction partners with which they can react chemically and form a stable covalent bond. On such textiles, the antimicrobial finish is durable. On polyester or polyamide, however, there are too few reaction partners to durably bind or bond such products.

When these textiles are washed, this antibacterial effect will usually disappear very largely or completely after just a few wash cycles.

It is an object of the present invention to provide a technical solution as to how quaternary ammonium compounds having a trimethoxysilylalkyl group on the quaternary ammonium group (or the hydrolysis forms thereof) can be applied in a manner which is very durable to washing to textiles made of synthetic fibers such as polyamide or polyester for example. There is a need for a composition which permits a durable antimicrobial finish and can be applied simply and inexpensively.

We have found that the abovementioned objects are achieved by a composition comprising an organic antimicrobial component (K) and at least one metal salt component (M) and also, where appropriate, a solvent (L) and, where appropriate, further auxiliary components, said organic component (K) comprising at least one compound of the general formula (I)

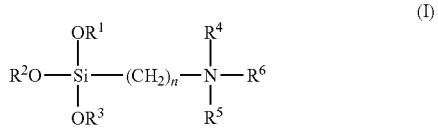
(I)

where the radicals independently have the following meanings, $R^1$ is a branched or unbranched alkyl radical which has 1 to 12 carbon atoms and may also be substituted by H—$((CH_2)_m$—$O)_q$, where m may be an integer from 0 to 4 and q is an integer from 1 to 6;

$R^2$ is a branched or unbranched alkyl radical which has 1 to 12 carbon atoms and may also be substituted by H—$((CH_2)_m$—$O)_q$, where m may be an integer from 0 to 4 and q is an integer from 1 to 6;

$R^3$ is a branched or unbranched alkyl radical which has 1 to 12 carbon atoms and may also be substituted by H—$((CH_2)_m$—$O)_q$, where m may be an integer from 0 to 4 and q is an integer from 1 to 6;

$R^4$ is a branched or unbranched alkyl radical having 1 to 18 carbon atoms, a cycloalkyl radical having 3 to 7 carbon atoms, a phenyl radical, a benzyl radical which is optionally substituted by one or two halogen atoms (for example dichlorobenzyl) or a heteroaryl radical;

$R^5$ is a branched or unbranched alkyl radical having 1 to 18 carbon atoms, a cycloalkyl radical having 3 to 7 carbon atoms, a phenyl radical, a benzyl radical which is optionally substituted by one or two halogen atoms, or a heteroaryl radical;

$R^6$ is a branched or unbranched alkyl radical having 8 to 18 carbon atoms;

n is an integer from 1 to 6, in particular from 1 to 4;

and said metal salt component (M) comprising at least one salt of a di- to pentavalent metal.

The organic component (K) comprises organosilicon ammonium compounds which may include any desired anion to balance the positive charge of the ammonium group. Examples of anions are halides (such as $F^-$, $CL^-$, $Br^-$), sulfates, carbonates, organic anions (such as acetate) and others.

Alkyl radical is to be understood as referring for example to a methyl, ethyl, propyl, butyl, hexyl, heptyl or octyl radical, but also, for example, the long-chain radicals such as octyl, decyl, dodecyl, tetradecyl, hexadecyl or octadecyl. These radicals may also be branched or unbranched, chiral or achiral.

The term cycloalkyl is to be understood as referring to mono- or bicyclic saturated groups having 3 to 8 carbon atoms, e.g., cyclohexyl, cyclopentyl or cyclopropyl, of which cyclohexyl is preferred.

The term "benzyl radical optionally substituted by one or two halogen atoms" is to be understood as meaning various mono- or disubstituted benzyl radicals which are substituted by fluorine, chlorine or bromine for example.

The term heteroaryl is to be understood as meaning mono- or bicyclic unsaturated radicals which comprise one or more "heteroatoms" (e.g., N, O or S). These radicals may comprise for example 6-membered and/or 5-membered rings. Examples of nitrogenous radicals are pyridine, pyrimidine, pyrazine, pyridazine, pyrrole, imidazole, triazole; of sulfur-containing radicals are thiophene or thiazole; and of oxygen-containing radicals are furan or oxazole.

Owing to the quaternary structure on the nitrogen atom, there is a positive charge in the molecule, which can be compensated by counterions for example. Typical anions in the salts are for example chloride, bromide, fluorides, hydrogensulfates, sulfates, phosphates, hydrogen-phosphates, formates, acetates or propionates. Preference is given to using chlorides.

Preference is given to a composition comprising as organic component (K) a compound of the general formula (I), where the radicals independently have the following meanings:

$R^1$ is an alkyl radical which has 1 to 6 carbon atoms and which may also be substituted by H—$((CH_2)_m$—$O)_q$, where m may be an integer from 1 to 3 and q is an integer from 1 to 4;

$R^2$ is an alkyl radical which has 1 to 6 carbon atoms and which may also be substituted by H—$((CH_2)_m$—$O)_q$, where m may be an integer from 1 to 3 and q is an integer from 1 to 4;

$R^3$ is an alkyl radical which has 1 to 6 carbon atoms and which may also be substituted by H—$((CH_2)_m$—$O)_q$, where m may be an integer from 1 to 3 and q is an integer from 1 to 4;

$R^4$ is an alkyl radical having 1 to 18 carbon atoms, a cycloalkyl radical having 3 to 7 carbon atoms, a phenyl radical, a benzyl radical optionally substituted by one or two halogen atoms, a pyridine radical, a pyrimidine radical, a pyrazine radical, a pyridazine radical, a pyrrole radical or an imidazole radical;

$R^5$ is an alkyl radical having 1 to 18 carbon atoms, a cycloalkyl radical having 3 to 7 carbon atoms, a phenyl radical, a benzyl radical, a pyridine radical, a pyrimidine radical, a pyrazine radical, a pyridazine radical, a pyrrole radical or an imidazole radical;

$R^6$ is an alkyl radical having 8 to 18 carbon atoms;

and n is an integer from 1 to 4.

Preference is given to using the compounds (K) in an aqueous solution.

As organic component (K) it is preferable to use a quaternary ammonium compound of the general formula (I), where the radicals independently have the following meanings:

$R^1$, $R^2$ and $R^3$ are each an alkyl radical which has 1 to 6 carbon atoms and which may also be substituted by $H-((CH_2)_m-O)_q$, where m may be an integer from 1 to 3 and q is an integer from 1 to 4; preferably it is methyl;

$R^4$ is an alkyl radical having 1 to 18 carbon atoms, a phenyl radical or a benzyl radical, $R^5$ is an alkyl radical having 1 to 18 carbon atoms;

$R^6$ is an alkyl radical having 8 to 18 carbon atoms;

and n is an integer from 2 to 4.

At least one of $R^4$, $R^5$ and $R^6$ in the general formula (I) should preferably be a long-chain, preferably unbranched alkyl radical having 10 to 18 carbon atoms for example.

The present invention also provides a composition comprising as organic component (K) a compound of the general formula (I), where $R^1$, $R^2$ and $R^3$ are the same and are each a branched or unbranched alkyl radical having 1 to 4 carbon atoms, in particular methyl, n is an integer from 1 to 4, in particular 3, $R^4$ is methyl, $R^5$ is alkyl having 1 to 12 carbon atoms, in particular methyl or decyl groups, and $R^6$ is alkyl having 8 to 18 carbon atoms, in particular decyl or octadecyl groups.

The compositions of the present invention are further characterized in that they comprise as metal salt component (M) at least one salt of a polyvalent, preferably divalent, trivalent or tetravalent metal. However, they may also contain small amounts of a 5-valent metal.

In one particular embodiment, they comprise as metal salt component (M) at least one salt of a divalent, trivalent or tetravalent metal from the group consisting of Mg, Ca, Ba, Zn, Sn; Al, Ga, Fe; and Ti.

As metal salt component (M) they may also comprise a salt of a divalent metal from the group consisting of Mg, Ca, Ba, Zn and/or a salt of a trivalent metal from the group consisting of Al and Fe, in which case the combination of a divalent salt and of a trivalent salt, for example the combination of a calcium salt and an aluminum salt, also gives good results.

Especially the combination of aluminum(III) salts with divalent metal salts will prove advantageous.

In one preferred embodiment, the present invention provides a composition which comprises as organic component (K) of the general formula (I) a dimethyltetradecyl-(3-(trimethoxysilyl)-propyl)ammonium salt, for example the chloride, or a dimethyloctadecyl-(3-(trimethoxysilyl)propyl)ammonium salt, for example a chloride, and as metal salt component (M) a salt of a divalent metal from the group consisting of Mg, Ca, Zn and/or a salt of a trivalent metal from the group consisting of Al and Fe.

Various anions, for example the chlorides, hydroxides, sulfates, phosphates and acetates, are useful as counterions in the metal salts.

The antimicrobial compositions of the present invention preferably contain two components (organic component (K) and metal salt component (M)) in defined amounts. Amounts are reported herein in % by weight. Textile pretreatment or aftertreatment compositions may be in solid, liquid or flowable form, for example as a gel, powder, granulate, paste or spray, and comprise the components of the present invention.

The amount of metal salt component (M) in the composition is preferably in the range from 0.01% to 10% by weight, more preferably in the range from 0.02% to 8% by weight, even more preferably in the range from 0.05% to 2.0% by weight and particularly in the range from 0.02% to 2.0% by weight, based on the overall composition.

The amount in which the organic component (K) is used is preferably in the range from 0.01% by weight to 10% by weight, preferably in the range from 0.02% to 8% by weight, more preferably in the range from 0.1% by weight to 3.0% by weight and particularly in the range from 0.3% by weight to 2.5% by weight, based on the overall weight of the composition.

The ratio between metal component (M) and organic component (K) is dependent on the metal salt used and ranges for example from 1:20 to 20:1, particularly from 1:10 to 10:1, in the antimicrobial composition, based on the molar amounts used. When, for example, a trivalent metal salt is used, then the ratio of the components is frequently in the range from 2:1 to 1:2 and particularly about 1:1. Preference is further given to using mixtures of di- and trivalent metal salts.

The composition of the present invention frequently comprises the following components:

0.01% to 10% by weight, in particular 0.05% to 2.0% by weight of the organic component (K) and 0.01% to 10% by weight, in particular 0.1% to 3% by weight of the metal salt component (M), and also 0% to 50% by weight, in particular 1% to 10% by weight of an organic solvent, for example alcohols (such as isopropanol).

Preference is given to a composition comprising:

0.3% to 2.5% by weight of the organic component (K) and 0.2% to 2.0% by weight of the metal salt component (M), 70% to 99.5% by weight of the solvent water, and also 0.1% to 30% by weight of auxiliary components.

The solvent used is preferably water and also additionally, where appropriate, an alcohol, for example ethanol, methanol, isopropanol or propanol. The preparations may also contain various auxiliary components, for example a pH buffer (such as sodium acetate) or an acid (such as formic acid or acetic acid).

In a further embodiment of the present invention, the composition further comprises, for example, one or more of the following auxiliaries: pH buffers, softeners, hydrophobicizers, oleophobicizers, binders, crosslinkers, flame retardants, textile dyes, sewability improvers and soil repellents.

The present invention also provides for the use of a composition as described above for antimicrobial and/or antiviral, but in particular antibacterial, finishing of textiles, fibers and yarns. The composition may also have antiviral activity.

Textiles, fibers and yarns of virtually any kind can be finished, particularly good results being even obtained on textiles, fibers and yarns containing synthetic materials or consisting of synthetic materials. Textiles, fibers and yarns composed of polyamide and/or polyester may be cited as examples.

The present invention also provides for the use of the above-described combination of a compound of the general formula (I) with a metal salt component (M) for antimicrobial finishing of textiles, fibers and yarns, for example by means of padding processes, foam application, spraying processes, coating (blade-coating processes for example) or exhaust method.

One composition as set out above can be used, but it is also possible to provide two or more preparations comprising the individual components, for example one preparation comprising the organic component of formula (I) and one preparation comprising the metal salt component.

The present invention also provides a process for preparing the abovementioned compositions, wherein the components are mixed.

The present invention provides in particular also for the use of a composition for antimicrobial and/or antiviral finishing of textiles, fibers and yarns containing synthetic materials or consisting of synthetic materials, for example products containing or consisting of polyamide and/or polyester.

Similarly, the textiles, fibers and yarns themselves finished with an antimicrobial (or antiviral) composition form part of the subject matter of the present invention.

Similarly, a process for antimicrobial (or antiviral) finishing of textiles, fibers and yarns forms part of the subject matter of the present invention, wherein at least one organic, antimicrobial component (K) of the general formula (I) and at least one metal salt component (M) as described above and also, where appropriate, solvent (L) and, where appropriate, further auxiliary components are applied to textiles, fibers or yarns at the same time or at different times.

The present invention also provides textiles, fibers and yarns finished with an antimicrobial (or antiviral) composition as described above or finished with the above-described combination of a compound of the general formula (I) with a metal salt component (M).

The described process for finishing fibers, yarns and/or textiles with an organic component (K) and a metal salt component (M) wherein these are applied to the fibers or textiles can be used in the manufacture of antimicrobial fibers, yarns and textiles. The antimicrobially (or antivirally) finished fibers can be used as starting product for diverse materials for various fiber products such as clothing (for example ladies' outerwear, menswear, children' wear, sports and leisure wear, workwear, socks, stockings and underwear), bedding (for example bed cover and sheets), home textiles, seat covers, upholstery fabrics, textiles for shoes, shower curtains, terry articles, wiping cloths, cleaning mops, filters, carpets, protective articles (for example mask and bandage) and the like.

The base fiber used in the present invention can be for example a natural or synthetic (manufactured) fiber. The natural fiber can be for example a vegetable fiber, such as cotton, hemp, flax, coir and reed. In principle, animal fibers, such as goats hair, mohair, cashmere, camel hair and silk and mineral fibers are also finishable with the process.

The manufactured fibers are for example cellulose fibers such as viscose fiber, regenerated, semisynthetic fibers, such as regenerated silk yarn or alginate fiber. Finishable synthetic fibers are in particular polyamide fiber, polyester fiber and their mixtures. In principle, the process of the present invention may also be applied to polypropylene fibers, polyvinyl fiber, polyacrylic fiber, polyurethane fiber, polyethylene fiber, polyvinylidene fiber and polystyrene fiber. The process may also be applied to blend fibers, however.

Polyamide and particularly polyester are contemplated as preferred target substrate, however. It is therefore a further object of the present invention to render the antimicrobial finishing of textiles to such as polyester more durable to washing. Durability to washing is said to be possessed by an antibacterial effect which is detectable after at least 20 wash cycles to EN ISO 6330 (6A) at 40° C. Detection is done by testing to JIS L 1902:2002 or to ASTM E 21-49 against, for example, *Staphylococcus aureus* ATCC 6538.

Microbe count reduction between finished and unfinished samples or between the finished sample after incubation and the microbe count of the inoculum should be about two powers of ten for antibacterial performance to be classified as good. Tests were also carried out in relation to antiviral performance.

The metal ions should be neither toxicologically nor ecotoxicologically relevant, nor shall they discolor the textile. The cations of the elements of the second and third main groups of the periodic table such as $Mg^{2+}$, $Ca^{2+}$, $Ba^{2+}$, $Al^{3+}$, $Ga^{3+}$, etc. and of the fourth main group such as, for example, $Ge^{4+}$ and $Sn^{4+}$ and $Ti^{4+}$ and of the transition groups such as for example $Zn^{2+}$, $Fe^{3+}$, $Al^{3+}$, $Sn^{2+}$, $Ti^{4+}$ appear to be most suitable.

In the experiments recited hereinbelow, calcium and aluminum prove to be particularly promising. At the same time, neither cation was observed to affect other textile chemicals, for example by causing discolorations or color changes.

The invention will now be more particularly elucidated by examples.

The commercially available product Sanitized T 99-19 is used; it comprises a 50% solution of dimethyltetradecyl[3-(trimethoxysilyl)]propylammonium chloride in the solvent methyl triglycol.

EXAMPLES 1-6

Amounts are specified in grams for the inventive compositions. Application is by padding onto Trevira polyester fabric having an areal weight of 220 g/m².

TABLE 1

| Bath make-up | 1 | 2 | 3 | 4 | 5 | 6 |
|---|---|---|---|---|---|---|
| water initially charged | 800 | 800 | 800 | 800 | 800 | 800 |
| aluminum chloride hexahydrate | 4.444 | 4.444 | 1.943 | 3.620 | 1.948 | 2.578 |
| sodium acetate | 4.528 | 4.528 | 1-.980 | 3.689 | 1.985 | 2.627 |
| calcium hydroxide | 1.278 | 1.278 | 2.430 | 1.667 | 2.438 | 2.147 |
| acetic acid 99% | 2.070 | 2.070 | 3.935 | 2.700 | 3.947 | 3.478 |
| Sanitized T 99-19 | 26.316 | 26.316 | 26.316 | 26.316 | 26.316 | 26.316 |
| isopropyl alcohol | 50 | 50 | 50 | 50 | 50 | 50 |
| mixtures are stirred at 200° C. for 30 min | | | | | | |
| pH set with formic acid to application by padder onto 220 g/m² polyester fabric | 6 | 4 | 5 | 5 | 3 | 3.75 |
| wet pick-up | 38.5% | 38.5% | 38.5% | 38.5% | 38.5% | 38.5% |
| drying temperature [° C.] | 120 | 120 | 120 | 120 | 120 | 120 |
| drying time [s] | 60 | 60 | 60 | 60 | 60 | 60 |
| cure temperature [° C.] | 150 | 150 | 150 | 150 | 150 | 150 |

TABLE 1-continued

| Bath make-up | 1 | 2 | 3 | 4 | 5 | 6 |
|---|---|---|---|---|---|---|
| cure time [s] | 120 | 120 | 120 | 120 | 120 | 120 |
| performance of finishes: | | | | | | |
| JISL 1902:2002 log kill rate for *Staphylococcus aureus* | | | | | | |
| finished and unwashed | 5.4 | 5.4 | 5.4 | 5.4 | 5.4 | 5.4 |
| finished and 10 washes (40° C.) | 5.4 | 5.4 | 5.4 | 2.3 | 5.4 | 5.4 |
| Kjeldahl nitrogen [mg/g] finished and 10 washes (40° C.) | 0.0251 | 0.0628 | 0.0477 | 0.0253 | 0.0851 | 0.0624 |

Further experiments with compositions similarly to examples 5 and 6 confirm the particularly good results in further experiments. Washing and testing is done in steps of ten at a time, up to 30 times. Microbe kill rate in each case is found to amount to at least 2 powers of ten by both methods (ASTM E 21-49 and by JIS L 1902:2002). A distinct antibacterial effect can be confirmed in the experiments.

A further investigation is carried out with the objective of making it easier for the user in the textile industry to prepare the compositions. The aim is to substantially simplify bath makeup in the dyehouse kitchens, where baths are normally prepared, so that fewer different chemicals, which moreover have to be metered pretty accurately, have to be used. This is intended, inter alia, to reduce the likelihood of mistakes and to significantly simplify the handleability of the recipes.

To this end, ready-to-use solutions are prepared by admixing a 5% aqueous solution of the product Sanitized T 99-19 with the appropriate amounts of aluminum chloride and calcium chloride, the acetate buffer and isopropanol. Such formulations are only stable for a few hours and separate thereafter. These formulations are sufficiently stable in less concentrated form, but less attractive as additives for the overall logistics because of packaging, transportation and storage costs.

This is why an attempt is made to separate the two solutions, that comprising the salts and the buffer, from that comprising the active compound, so that the user has to handle two solutions (kit-of-parts). For solubility reasons, a further experiment was carried out in which the moderately soluble calcium hydroxide is replaced by the very readily soluble calcium chloride.

An attempt was also made to replace the organic solvent isopropyl alcohol by water. To further simplify the system, a further experiment seeks to omit the acetate buffer from the system, without replacing it.

EXAMPLE 7

971.6 g water (tap water) are initially charged. Then 7.5 g of aluminum chloride hexahydrate (CAS: 7784-13-6), 14.0 g of calcium chloride (CAS: 10043-52-4), 2.0 g of sodium acetate trihydrate (CAS: 6131-90-4) and 4.9 g of 80% acetic acid (CAS 64-19-7) are added in succession with stirring. Of this solution, 150 g are added to 835 g of water, and 15 g of Sanitized T 99-15 are added with stirring. After 30 minutes of stirring at room temperature, the clear solution is padded onto white polyester fabric. The wet pick-up is 45% and therefore the pick-up of Sanitized T 99-19 is 0.67%.

Application is repeated for the same solution after standing at room temperature for 4 hours, 24 hours and 48 hours. Interestingly, the bath is cloudy after 48 hours.

The finished textiles are tested against *Staphylococcus aureus* to ASTM E 21-49. All specimens display good to excellent performance against the bacteria even after 30 wash cycles.

EXAMPLE 8

921.6 g water (tap water) are initially charged. Then, 7.5 g of aluminum chloride hexahydrate (CAS: 7784-13-6), 14.0 g of calcium chloride (CAS: 10043-52-4), 2.0 g of sodium acetate trihydrate (CAS: 6131-90-4), 4.9 g of 80% acetic acid (CAS 64-19-7) and 50 g of isopropyl alcohol (CAS: 67-63-0) are added in succession with stirring. Of this solution, 150 g are added to 835 g of water, and 15 g of Sanitized T 99-19 are added with stirring. After 30 minutes of stirring at room temperature, the clear solution is padded onto white polyester fabric. The wet pick-up is 45% and therefore the pick-up of Sanitized T 99-19 is 0.67%. Application is repeated for the same solution after standing at room temperature for 4 hours, 24 hours and 48 hours. Interestingly, the bath is cloudy after about 48 hours.

The finished textiles are tested against *Staphylococcus aureus* to ASTM E 21-49. All specimens display good to excellent performance against the bacteria even after 30 wash cycles. The result does not show relevant differences to example 7.

Therefore, isopropyl alcohol is not necessary for this application and can be employed for special cases such as superhydrophobic coatings.

EXAMPLE 9

978.5 g water (tap water) are initially charged. Then, 7.5 g of aluminum chloride hexahydrate (CAS: 7784-13-6), and 14.0 g of calcium chloride (CAS: 10043-52-4) are added in succession with stirring. Of this solution, 150 g are added to 835 g of water, and 15 g of Sanitized T 99-19 are added with stirring. After 30 minutes of stirring at room temperature, the clear solution is padded onto white polyester fabric. The wet pick-up is 45% and therefore the pick-up of Sanitized T 99-19 is 0.67%. Application is repeated for the same solution after standing at room temperature for 4 hours, 24 hours and 48 hours. Interestingly, the bath is cloudy after just around 4 hours.

The finished textiles are tested against *Staphylococcus aureus* to ASTM E 21-49. All specimens display good to excellent performance against the bacteria even after 30 wash cycles. However, the results are less positive than those of examples 7 and 8. Nothing found here is relevant to the buffering system, in particular since the solution gives an acidic reaction even without the acetate buffer.

EXAMPLES 10 TO 12

Experiments with an aqueous solution of dimethyloctadecyl-[3-(trimethoxysilyl)propyl]-ammonium chloride are carried out similarly to examples 7 to 9, using, per 150 g of the solution of the quaternary ammonium salt, 130 g of the salt solutions with and without isopropanol and with and without acetate buffer.

These baths were cloudy from the start and have a distinctly higher viscosity than those of examples 7 to 9, but are applied in that state and tested. After 20 wash cycles, the products display an adequate to good antibacterial performance.

EXAMPLE 13

27.8 g of aluminum chloride hexahydrate are dissolved in 965.3 g of water and admixed with 2.0 g of sodium acetate trihydrate and 4.9 g of 80% acetic acid. The solution is stirred on a magnetic stirrer at room temperature for 5 minutes. 835 g of water are initially charged and 15 g of Sanitized T 99-19 are added, the mixture is briefly stirred, and then admixed with 150 g of the aluminum chloride solution, followed by stirring on the magnetic stirrer at room temperature for 30 minutes.

This liquor is padded onto polyester fabric and the fabric is subsequently dried on the tenter at 120° C. and the specimens thus obtained are washed 10, 20 or 30 times at 40° C. and subsequently to tested against *Staphylococcus aureus* ATCC 6538 to ASTM E 21-49. The results show a bacterial kill factor of above 100 compared with the unfinished control specimen.

EXAMPLE 14

7.5 g of aluminum chloride hexahydrate and 30.8 g of barium chloride dihydrate (CAS: 10326-27-9) are dissolved in 954.8 g of water and admixed with 2.0 g of sodium acetate trihydrate and 4.9 g of 80% acetic acid. The solution is stirred on a magnetic stirrer at room temperature for 5 minutes. 835 g of water are initially charged and 15 g of Sanitized T 99-19 are added, the mixture is briefly stirred, then 150 g of the salt/acetate buffer solution are added, followed by stirring on the magnetic stirrer at room temperature for 30 minutes.

This liquor is padded onto polyester fabric and the fabric is subsequently dried on the tenter at 120° C. and the specimens thus obtained are washed 10, 20 or 30 times at 40° C. and subsequently tested against *Staphylococcus aureus* ATCC 6538 to ASTM E 21-49. The results show a bacterial kill factor of above 100 compared with the unfinished control specimen.

EXAMPLE 15

7.5 g of aluminum chloride hexahydrate and 25.6 g of magnesium chloride hexahydrate (CAS: 7791-18-6) are dissolved in 960 g of water and admixed with 2.0 g of sodium acetate trihydrate and 4.9 g of 80% acetic acid. The solution is stirred on a magnetic stirrer at room temperature for 5 minutes. 835 g of water are initially charged and 15 g of Sanitized T 99-19 are added, the mixture is briefly stirred, then 150 g of the salt/acetate buffer solution are added, followed by stirring on the magnetic stirrer at room temperature for 30 minutes.

This liquor is padded onto polyester fabric and the fabric is subsequently dried on the tenter at 120° C. and the specimens thus obtained are washed 10, 20 or 30 times at 40° C. and subsequently tested against *Staphylococcus aureus* ATCC 6538 to ASTM E 21-49. The results show a bacterial kill factor of above 100 compared with the unfinished control specimen.

EXAMPLE 16

7.5 g of aluminum chloride hexahydrate and 27.6 g of zinc acetate dihydrate (CAS: 5970-45-6) are dissolved in 958 g of water and admixed with 2.0 g of sodium acetate trihydrate and 4.9 g of 80% acetic acid. The solution is stirred on a magnetic stirrer at room temperature for 5 minutes.

835 g of water are initially charged and 15 g of Sanitized T 99-19 are added, the mixture is briefly stirred, then 150 g of the salt/acetate buffer solution are added, followed by stirring on the magnetic stirrer at room temperature for 30 minutes. This liquor is padded onto polyester fabric and the fabric is subsequently dried on the tenter at 120° C. and the specimens thus obtained are washed 10, 20 or 30 times at 40° C. and subsequently tested against *Staphylococcus aureus* ATCC 6538 to ASTM E 21-49.

The results show a bacterial kill factor of above 100 compared with the unfinished control specimen.

EXAMPLE 17

42.2 g of barium chloride dihydrate are dissolved in 950.9 g of water and admixed with 2.0 g of sodium acetate trihydrate and 4.9 g of 80% acetic acid. The solution is stirred on a magnetic stirrer at room temperature for 5 minutes.

835 g of water are initially charged and 15 g of Sanitized T 99-19 are added, the mixture is briefly stirred, then 150 g of the salt/acetate buffer solution are added, followed by stirring on the magnetic stirrer at room temperature for 30 minutes. This liquor is padded onto polyester fabric and the fabric is subsequently dried on the tenter at 120° C. and the specimens thus obtained are washed 10, 20 or 30 times at 40° C. and subsequently tested against *Staphylococcus aureus* ATCC 6538 to ASTM E 21-49. The results show a bacterial kill factor of above 100 compared with the unfinished control specimen.

EXAMPLE 18

19.2 g of calcium chloride are dissolved in 973.9 g of water and admixed with 2.0 g of sodium acetate trihydrate and 4.9 g of 80% acetic acid. The solution is stirred on a magnetic stirrer at room temperature for 5 minutes.

835 g of water are initially charged and 15 g of Sanitized T 99-19 are added, the mixture is briefly stirred, then 150 g of the salt/acetate buffer solution are added, followed by stirring on the magnetic stirrer at room temperature for 30 minutes.

This liquor is padded onto polyester fabric and the fabric is subsequently dried on the tenter at 120° C. and the specimens thus obtained are washed 10, 20 or 30 times at 40° C. and subsequently tested against *Staphylococcus aureus* ATCC 6538 to ASTM E 21-49.

The results show a bacterial kill factor of above 100 compared with the unfinished control specimen.

EXAMPLE 19

35.0 g of magnesium chloride hexahydrate are dissolved in 958.1 g of water and admixed with 2.0 g of sodium acetate trihydrate and 4.9 g of 80% acetic acid. The solution is stirred on a magnetic stirrer at room temperature for 5 minutes.

835 g of water are initially charged and 15 g of Sanitized T 99-19 are added, the mixture is briefly stirred, then 150 g of the salt/acetate buffer solution are added, followed by stirring on the magnetic stirrer at room temperature for 30 minutes. This liquor is padded onto polyester fabric and the fabric is subsequently dried on the tenter at 120° C. and the specimens thus obtained are washed 10, 20 or 30 times at 40° C. and subsequently tested against *Staphylococcus aureus* ATCC 6538 to ASTM E 21-49. The results show a bacterial kill factor of above 100 compared with the unfinished control specimen.

EXAMPLE 20

37.8 g of zinc acetate dihydrate are dissolved in 958.1 g of water and admixed with 2.0 g of sodium acetate trihydrate and 4.9 g of 80% acetic acid. The solution is stirred on a magnetic stirrer at room temperature for 5 minutes.

835 g of water are initially charged and 15 g of Sanitized T 99-19 are added, the mixture is briefly stirred, then 150 g of the salt/acetate buffer solution are added, followed by stirring on the magnetic stirrer at room temperature for 30 minutes. This liquor is padded onto polyester fabric and the fabric is subsequently dried on the tenter at 120° C. and the specimens thus obtained are washed 10, 20 or 30 times at 40° C. and subsequently tested against *Staphylococcus aureus* ATCC 6538 to ASTM E 21-49. The results show a bacterial kill factor of above 100 compared with the unfinished control specimen.

EXAMPLE 21

971.6 g of water (tap water) are initially charged. Then 75 g of aluminum chloride hexahydrate, 140 g of calcium chloride, 20 g of sodium acetate trihydrate and 49 g of 80% acetic acid are added in succession with stirring, with the solution heating up significantly during the additions and dissolution of the salts. Of this solution, 20 g are added to 960 g of water, and 20 g of Sanitized T 99-15 are added with stirring. After 30 minutes of stirring at room temperature, the clear solution is padded onto white polyester fabric. The wet pick-up is 45% and therefore the pick-up of Sanitized T 99-19 is 0.67%. Application is repeated for the same solution after standing at room temperature for 4 hours, 24 hours and five days. The bath is cloudy after about 48 hours.

The finished textiles are tested against *Staphylococcus aureus* to ASTM E 21-49. All specimens display good to excellent performance against the bacteria even after 30 wash cycles.

EXAMPLE 22

400 g of water are initially charged and then 0.37 g of aluminum chloride hexahydrate, 0.99 g of sodium acetate trihydrate, 0.47 g of calcium hydroxide, 2.47 g of 80% acetic acid, 5.07 g of Sanitized T 99-19 and 25 g of isopropanol are dissolved therein in succession. The pH is adjusted to 3 with formic acid, and the bath is stirred at room temperature for 30 minutes. Then, 32.5 g of Arkofix NES liq, a modified dimethyloldihydroxy ethylene urea derivative, an extremely low-formaldehyde crosslinker for low-iron or no-iron finishing of cellulose fibers from the manufacturer Clariant (Switzerland) are added, followed by 4 g of 50% magnesium chloride hexahydrate solution in water, 7.5 g of Ceranin HDP liq, an amphoteric softener based on polyethylene, 7.5 g of Ceraperm SAP liq, an permanent nonionic softener.

Based on microsiloxane and polyethylene and Leucophor BLR liq optical brightener, an anionic stilbene derivative, and like all other textile chemicals used, likewise from the manufacturer Clariant.

Water is used to top up to 500 g. This bath is padded onto a textile consisting mainly of polyester and cotton, such that 0.6% of Sanitized T 99-19 end up on the final fabric, corresponding to a wet pick-up of 60%. The textile is tenter dried and cured at 150° C. such that the temperature was held at the final temperature for two minutes.

This textile, which is typically used for workwear, is washed 50 times at 60° C. and tested after every 10 wash cycles. After 50 washes, a microbe kill rate of $10^{2.5}$ is achieved in the ASTM E 21-49 test, an excellent value. Virtually the same microbe kill rate is achieved (102.8) when the textile is treated at 175° C. for an effective cure time of 30 seconds.

EXAMPLE 23

A fabric finished by following examples 5 and 21 is admixed with a suspension of viruses (MS2 coatless phages) in a concentration of $10^5$ viruses per ml. The concentration of viruses decreases from 20 000 and 25 000 to zero within 60 minutes. This drastic reduction in virus count shows that the preparations have virucidal properties.

EXAMPLE 24

First the salt solution (SL) is prepared as follows:

6.0 liters of water are initially charged and then 750 grams of aluminum chloride hexahydrate, 2.56 kilograms of magnesium chloride hexahydrate, 200 grams of sodium acetate trihydrate and 490 grams of acetic acid (80%) are dissolved therein in succession. This solution is designed such that it can be used 1:1 with the Sanitized T 99-19 antibacterial product.

982 grams of water are initially charged and then 8.0 grams of the salt solution (SL), 8.0 grams of Sanitized T 99-19 and 1.0 gram of Hostapal MRN nonionic wetting agent (from Clariant, Switzerland) and 1.0 gram of acetic acid (80%) are added in succession with stirring. The homogeneous solution is left to stand at room temperature for one hour. A padder is used to apply this solution to an orange textile composed of purely polyester and having an areal weight of about 133 grams per square meter.

Wet pick-up is 79% and therefore the concentration of the Sanitized T 99-19 and of the salt solution (SL) is 0.63% each, based on the mass of the dry textile. The textile is dried for 60 seconds at 130° C., measured on the textile surface. The specimens are tested by the ASTM E 21-49 method against *Staphylococcus aureus* ATCC 6538 immediately after finishing and after 20 wash cycles to EN ISO 6330 (6A) at 40° C. The decadic logarithm of the microbe kill rate is above 3.7 for the unwashed specimen and 2.6 for the specimen washed 20 times. These values correspond to microbe kill rates of greater than 5000 and 400, respectively, compared with the inoculum, which are excellent values.

EXAMPLE 25

A steel vessel is initially charged with 46 kilograms of water, followed by 500 grams of the salt solution (SL) of example 24 being added with stirring and subsequently 50 grams of Sanitized T 99-19 being added with stirring. This liquor is left to stand at room temperature for one hour, and subsequently 2.0 kilograms of Nuva TTC (a slightly cationic fluorocarbon for oil and water repellency of textiles, manufacturer: Clariant, Switzerland) and 500 grams of Cassurit FF (a nonionic wetting agent to improve the durability of oil and water-repellent textile finishes, manufacturer: Clariant) are stirred into the liquor in succession.

Liquor pH is adjusted to 4.2 with acetic acid, and the liquor is immediately padded onto a white laboratory apparel blend fabric composed of 65% polyester and 35% cotton and having an areal weight of 90 grams per square meter. Wet pick-up is 73%, which corresponds to an applied to amount of 0.73% of Sanitized T 99-19 and 0.73% of the salt solution (SL). The fabric is dried and cured on an 18 meter tenter at 180° C. (temperature of panels) at a speed of 15 meters per minute.

Antimicrobial efficacy is tested to ASTM E 21-49 against *Staphylococcus aureus* ATCC 6538 after 100 wash cycles to EN ISO 6330 (3A) 60° C. Microbe kill rate is $10^{2.2}$ (a factor of around 160) compared with the inoculum.

EXAMPLES 26-30

Laboratory recipes were established for five different fabrics for sports underwear composed of polyester (PES) and in some instances with wool (WO). Application is to prewashed fabric by padding, and drying is on a tenter with IR temperature measurement on the textile surface.

Drying time was 60 seconds each at the 120° C. surface temperature of the textile. Antibacterial efficacy is tested to ASTM E 21-49 against *Staphylococcus aureus* ATCC 6538 after 25 wash cycles to EN ISO 6330 (6A).

TABLE 2

|  | 100% PES, Art. 28387 light gray | 74% PES, 26% WO, black | 100% PES, Art. 89479 light gray | 80% PES, 20% WO black | 77% PES 23% WO dark gray |
|---|---|---|---|---|---|
| acetic acid 80% | 0.5 g/l | 0.5 g/l | 0.5 g/l | 0.5 g/l | 0.5 g/l |
| Hostapal MRN liq | 0.5 g/l | 0.5 g/l | 0.5 g/l | 0.5 g/l | 0.5 g/l |
| Sanitized ® T 99-19 | 8.0 g/l | 8.0 g/l | 8.0 g/l | 8.0 g/l | 8.0 g/l |
| RP 26-19 (13) | 8.0 g/l | 8.0 g/l | 8.0 g/l | 8.0 g/l | 8.0 g/l |
| pH adjusted with acetic acid | 4.5-5 | 4.5-5 | 4.5-5 | 4.5-5 | 4.5-5 |
| wet pick-up | 77% | 77% | 76% | 75% | 75% |
| level of Sanitized ® T 99-19 test | 0.61% | 0.61% | 0.60% | 0.60% | 0.60% |
| log kill rate after 25 washes | >3.8 | 2.6 | >3.8 | 2.3 | 2.0 |

EXAMPLE 31

Undyed fabric having an areal weight of 133 grams per square meter and composed of purely polyester microfiber, the high specific surface area of the fabric making it particularly difficult to provide with wash-durable finishes using any kind of finishing product, is finished with Sanitized T 99-19 and the salt mixture as described hereinbelow:

984 grams of water are initially charged, 8.0 grams of the salt solution (SL) of example 24 are added with stirring, followed by 8.0 grams of Sanitized T 99-19 added with stirring until a homogeneous solution is formed. The pH is adjusted to 4.5 with acetic acid. The solution is left to stand at room temperature for one hour and then padded onto the microfiber fabric. Wet pick-up is 85% and therefore the pick-up is 0.68% each for the Sanitized T 99-19 and the salt solution.

The specimen is tenter dried and cured at 150° C. for 90 seconds. The test against *Staphylococcus aureus* ATCC 6538 and against *Klebsiella pneumoniae* ATCC 4352 is carried out after 20 EN ISO 6330 (6A) 40° C. wash cycles. Microbe kill rate is $10^{3.2}$ (a factor of 1600) for *Staphylococcus* and $10^{1.8}$ (a factor of 60) for *Klebsiella* compared with the inoculum.

The identical control finish yielded $10^{>3.2}$ after 20 washes, and after 30 and after 40 wash cycles the kill rate for the Staphylococcae was still $10^{3.1}$ (factor of 1250) compared with the inoculum.

The same textile dyed brown before finishing in an identical manner likewise achieved a kill rate of $10^{3.1}$ (factor 1250) after 30 wash cycles and still $10^{12}$ after 40 wash cycles, compared with the inoculum.

EXAMPLE 32

Influence of Bath Standing Time Before Application on Wash Durability of Finish

Application solutions are prepared in an identical manner to the description of experiment 31 and left to stand for 1 hour, 6 hours and 24 hours at room temperature before application to polyester fabric and to polyamide by padding and testing against *Staphylococcus aureus* ATCC 6538 to ASTM E 21-49 after 15, 20 and 25 wash cycles. All the samples gave good antibacterial performance and no difference whatever can be detected between the individual applications.

This experiment is repeated except that the liquor pH is adjusted to 3 with formic acid and the liquor was applied after 5 days. In addition to the 100% Trevira polyester, 220 grams per square meter fabric of example 32, a second style was finished, Dacron 54 spun, 120 grams per square meter. The specimens are washed up to 30 wash cycles. In this series of experiments, all specimens gave a microbe kill rate of at least factor 80 after 30 wash cycles, without any differences between the specimens beyond experimental scatter.

What is claimed is:

1. A composition comprising an organic antimicrobial component (K), at least one metal salt component (M), optionally a solvent (L) and, optionally auxiliary components, said organic component (K) comprising at least one compound of the general formula (I)

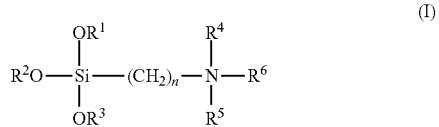

where the radicals independently have the following meanings:
$R^1$, $R^2$, and $R^3$ are the same and are each a branched or unbranched alkyl radical having 1 to 4 carbon atoms,
$R^4$ is methyl
$R^5$ is an alkyl having 1 to 12 carbon atoms
$R^6$ is an alkyl having 8 to 18 carbon atoms
n is an integer from 1 to 4,
said metal salt component (M) comprising at least one salt of a divalent, trivalent, or tetravalent metal selected from the group consisting of Mg, Ca, Ba, Zn, Sn, Al, Ga, Fe, and Ti, and
wherein the ratio between the metal salt component (M) and the organic component (K) is from 1:10 to 10:1 based on the molar amounts used.

2. The composition as claimed in claim 1, wherein it comprises as metal salt component (M) a salt of a divalent metal from the group consisting of Mg, Ca, Ba, Zn and/or a salt of a trivalent metal from the group consisting of Al and Fe.

3. The composition as claimed in claim 1, wherein it comprises as organic component (K) of the general formula (I) a dimethyltetradecyl-(3-(trimethoxysilyl)-propyl)ammonium salt or a dimethyloctadecyl-(3-(trimethoxysilyl)propyl)ammonium salt and as metal salt component (M) a salt of a divalent metal from the group consisting of Mg, Ca, Zn, Ba and/or a salt of a trivalent metal from the group consisting of Al and Fe.

4. The composition as claimed in claim 1, wherein it represents an aqueous solution comprising 0.01% to 10% by weight, of the organic component (K) and 0.01% to 10% by weight of the metal salt component (M) and also 0% to 50% by weight of an organic solvent.

5. The composition as claimed in claim 1, wherein it comprises 0.3% to 2.5% by weight of the organic component (K) and 0.2% to 2.0% by weight of the metal salt component (M), 70% to 99.5% by weight of water as solvent (L) and also 0.1% to 30% by weight of auxiliary components.

6. The composition as claimed in claim 1, wherein it comprises as solvent water and also, optionally, an alcohol and optionally an auxiliary component, selected from the group consisting of pH buffers, softeners, hydrophobicizers, oleophobicizers, binders, crosslinkers, flame retardants, textile dyes, sewability improvers, soil repellents and combinations thereof.

7. Textiles, fibers and yarns finished with an antimicrobial and/or antiviral composition as claimed in claim 1.

8. Textiles, fibers and yarns finished with an antimicrobial composition as claimed in claim 1.

9. A process for antimicrobial and/or antiviral finishing of textiles, fibers and yarns, which comprises at least one organic antimicrobial component (K) of the general formula (I) as set forth in claim 1 and at least one metal salt component (M) as set forth in claim 1 and also, where appropriate, solvent (L) and, where appropriate, further auxiliary components being applied to textiles, fibers and yarns at the same time or at different times.

10. A process for finishing textiles, fibers and yarns comprising polyamide and/or polyester as claimed in claim 9.

11. A process for finishing textiles, fibers and yarns by means of padding processes, foam application, spraying processes, coating or exhaust method as claimed in claim 9.

* * * * *